(12) United States Patent
Nesaretnam et al.

(10) Patent No.: US 8,906,960 B2
(45) Date of Patent: Dec. 9, 2014

(54) SYNERGISTIC EFFECT OF TOCOTRIENOLS AND CURCUMIN

(75) Inventors: Kalanithi Nesaretnam, Selangor (MY); Kanga Rani Selvaduray, Selangor (MY)

(73) Assignee: Malaysian Palm Oil Board, Selangor (MY)

( * ) Notice: Subject to any disclaimer, the term of this patent is extended or adjusted under 35 U.S.C. 154(b) by 0 days.

(21) Appl. No.: 13/582,477

(22) PCT Filed: Mar. 8, 2011

(86) PCT No.: PCT/MY2011/000019
§ 371 (c)(1),
(2), (4) Date: Sep. 4, 2012

(87) PCT Pub. No.: WO2011/112071
PCT Pub. Date: Sep. 15, 2011

(65) Prior Publication Data
US 2012/0329864 A1    Dec. 27, 2012

(30) Foreign Application Priority Data

Mar. 8, 2010   (MY) ............................ PI2010000993

(51) Int. Cl.
- *A61K 31/355* (2006.01)
- *A61K 31/05* (2006.01)
- *A61P 35/00* (2006.01)
- *A61K 31/045* (2006.01)

(52) U.S. Cl.
CPC ............. *A61K 31/045* (2013.01); *A61K 31/355* (2013.01); *A61K 31/05* (2013.01)
USPC ........... 514/458; 514/733; 514/734; 514/717; 514/718; 514/720; 549/408; 568/729

(58) Field of Classification Search
CPC ............ A61K 2300/00; A61K 31/355; A61K 36/9066; A61K 31/09; A61K 2800/522; A23V 2200/308; A23V 2250/2112; A23V 2250/712
USPC ................. 514/458, 733, 734, 717, 718, 720; 549/408; 568/729
See application file for complete search history.

(56) References Cited

U.S. PATENT DOCUMENTS

| | | |
|---|---|---|
| 2004/0116514 A1 | 6/2004 | Nishino et al. |
| 2005/0095301 A1 | 5/2005 | Deshpande |
| 2006/0216251 A1 | 9/2006 | Morariu |
| 2006/0251750 A1* | 11/2006 | Tabor ............................ 424/757 |
| 2008/0175888 A1* | 7/2008 | Lindemann et al. .......... 424/442 |

OTHER PUBLICATIONS

Definition of prevent, Princeton University "About WordNet." WordNet. Princeton University. 2010. <http://wordnet.princeton.edu> accessed Sep. 18, 2012.*
Sosa et al. Ageing Research Reviews 2013, 12, 376-390.*
Wilken et al. Molecular Cancer 2011, 10 (12), 1-19.*
Webb Biochemical Pharmacology 2014, 87, 121-130.*
National Cancer Institute at the National Institutes of Health, A to Z List of Cancers, http://www.cancer.gov/cancertopics/types/alphalist/b accessed Apr. 8, 2014.*
Guthrie et al. Journal of Nutrition 1997, 127, 544S-548S.*

* cited by examiner

*Primary Examiner* — Sreeni Padmanabhan
*Assistant Examiner* — Irina Neagu
(74) *Attorney, Agent, or Firm* — Greer, Burns & Crain, Ltd.

(57) ABSTRACT

A transdermal fluid is provided wherein the main ingredient is tocotrienol and curcumin is added to enhance the anti-cancer effects of tocotrienols. The composition is useful for the treatment or prevention of a cancer, a tumor or an inflammatory disorder, particularly breast cancer.

4 Claims, 2 Drawing Sheets

SYNERGISTIC EFFECT OF TOCOTRIENOLS AND CURCUMIN

The present application is a National Stage application of International Application No. PCT/MY2011/000019 filed on Mar. 8, 2011, which claims priority to and the benefit of Malaysian Patent Application No. PI 2010000993 filed on Mar. 8, 2010.

FIELD OF INVENTION

The present invention relates to a transdermal fluid wherein the main ingredient is tocotrienol; and curcumin is the supporting ingredient.

BACKGROUND ART

Breast cancer worldwide affects nearly one million women per year and although current treatments do help many patients, more than 350,000 die from the disease. In Malaysia, breast cancer is the most common cancer where the statistic shows that 18.0% of the total cancer case reported is from breast cancer. It is documented that 11,952 new breast cancer cases were reported to the National Cancer Registry within year 2003-2005, which comprised 31.3% of all cancers in women.

The established risk factors for breast cancer include a family history of breast cancer, early menarche, late age at first childbirth, late age at menopause and history of benign breast disease. With the exception of the genetic predisposition to the disease the rest of the risk factors point to the life time exposure of women to estrogen. Estrogen does not cause the disease but is involved in the progression and development of breast cancer. Anti-estrogens are therefore used as therapy in the control of breast cancer progression.

Scientific investigations have been undertaken to associate possible functional properties, antioxidant or otherwise in the diet, which could be efficient in preventing diseases like cancer. One such antioxidant is vitamin E. The tocotrienol (or T3) group together with tocopherols compose the vitamin E family. Both have four isomers, which are α-, β-, γ-, δ-tocopherols and α-, β-, γ-, δ-Tocotrienols (Machlin et al., 1991).

The major structural difference of tocotrienol from tocopherol is through its unsaturated side chain that has three double bonds in its farnesyl isoprenoid tail. Tocotrienols also display a variety of functions that are clearly distinct from that of α-tocopherols (Sen et al., 2006) Tocopherols are abundant in common vegetables and nuts, while tocotrienols can be found in rice bran, wheat germ and most abundantly in the fruit of palm (Sundram, et al., 2002; Sookwong, et al., 2007). Crude palm oil extracted from the fruits of oil palm (*Elaeis guineensis*) particularly contains a larger concentration of tocotrienols (up to 800 mg kg$^{-1}$) than all other natural sources (Theriault et al., 1999). The tocotrienol-rich fractions (TRF) composed of 32% α-tocopherol and 68% tocotrienols can be obtained from palm oil after esterification and following distillation, crystallization and chromatography (Sundram et al., 1992).

Tocotrienol isomers of vitamin E in palm oil have been reported to contain biological and physiological properties which include potential blood cholesterol lowering and cardioprotective effects, efficient antioxidant activity in biological systems, and possible anticancer and neuroprotective effects (Sen et al., 2006).

Previous studies showed that tocotrienols are the components of vitamin E responsible for growth inhibition in human breast cells in vitro as well as in vivo (Nesaretnam et al., 1998). The inhibitory effects on cancer cell growth was found to be different in the four isomers of tocotrienols with studies reported that γ- and δ-tocotrienols have pronounced inhibitory effect compared to α- and β-tocotrienol (Yu et al., 1999). TRF and δ- and γ-tocotrienol are shown to inhibit the proliferation of PC-3, a prostate cancer cell whereas α-tocopherol showed no significant effects (Nesaretnam et al., 2008). Various findings have demonstrated the superiority of tocotrienols over tocopherols in terms of their anti-cancer property. Tocotrienols, but not tocopherols, inhibited the growth of normal mouse mammary epithelial cells, ZR-75-1, a responsive human breast cancer line and MDA-MD-435 oestrogen-receptor-negative human breast cancer cells (McIntyre et al., 2000; Nesaretnam et al., 2000; Nesaretnam et al., 1995). Noguchi and colleagues (2003) reported that α-tocotrienol suppresses the expression of vascular cell adhesion molecule-1 (VCAM-1) and the adhesion of THP-1 monocytic cells to human umbilical vein endothelial cells (HUVECs). In fact, the efficacy shown by α-tocotrienol was 10-fold higher than that of α-tocopherol. In addition, α-tocotrienol also exhibits neuroprotective activities through its protection against glutamate- and stroke-induced neurodegeneration, a property not seen in α-tocopherol (Khanna et al., 2005).

In recent years, the medicinal properties of turmeric and its bioactive compound curcumin have increasingly been recognized. Curcumin, a bioactive constituent derived from the rhizomes of *Curcuma longa* is one of the major yellow pigments found in turmeric and has over many years of history in traditional medicinal uses. There are many evidences for its cytotoxic, antiproliferative, and/or proapoptotic activity toward neoplastic cells in vitro, and suppression of tumorigenesis in rodent models (Sharma et al., 2005; Duvoiz et al., 2005; Aggarwal et al., 2005). These findings further give ways for curcumin's translation into therapeutic modalities to combat cancer. Previous study has shown curcumin potentiates the growth inhibitory effect of celecoxib by shifting the dose-response curve to the left. The synergistic growth inhibitory effect was mediated through a mechanism that probably involves inhibition of the COX-2 pathway and may involve other non COX-2 pathways (Lev-Ari et al., 2005). Extracellularly, curcumin acts as a strong antioxidant (Subramaniam et al., 1994; Mukundan et al., 1993) an anti-inflammatory agent and reduces free radical production (Huang et al., 1991). Curcumin is a small, lipophilic molecule that can pass through the cell membranes and exert intracellular effects as well. Curcumin's most observed property is its pronounced anti-proliferative action, described in several cell types, including colon (Ramsewak et al., 2000) and microglial (Lim et al., 2001) cells as well as its ability to induce apoptosis in cancer cells (Ruby et al., 1995). Curcumin also known to disrupts the conformation of the p53 protein required for its serine phosphorylation, its binding to DNA, its transactivation of p53-responsive genes and p53-mediated cell cycle arrest (Moss et al., 2004). Menon et al (1995) reported that curcumin-induced inhibition of B16F-10 melanoma lung metastasis in mice. Oral administration of curcumin at concentrations of 200 nmol/kg body weight reduced the number of lung tumor nodules by 80%. The life span of the animals treated with curcumin was increased by 143.85% (Menon et al., 1995).

SUMMARY OF INVENTION

In one embodiment of the present invention is a composition containing an active amount of tocotrienol or derivative thereof as the main ingredient; and an addition of curcumin, for prevention or inhibition of a cancer and/or a tumour in a mammal, preferably breast cancer, wherein curcumin is added to the composition to enhance the anti-cancer effect in tocotrienol.

Further, there is also provided a composition containing an active amount of tocotrienol or derivative thereof as the main ingredient; and an addition of curcumin, for prevention or treatment of an inflammatory disorder in a mammal.

The present invention consists of several novel features and a combination of parts hereinafter fully described and illustrated in the accompanying drawings, it being understood that various changes in the details may be made without departing from the scope of the invention or sacrificing any of the advantages of the present invention.

It is to be noted that tocotrienols have potent anti-cancer effects and the addition of curcumin enhances the anti-cancer effect in tocotrienols.

BRIEF DESCRIPTION OF THE ACCOMPANYING DRAWINGS

To further clarify various aspects of some embodiments of the present invention, a more particular description of the invention will be rendered by references to specific embodiments thereof, which are illustrated, in the appended drawings. It is appreciated that these drawings depict only typical embodiments of the invention and are therefore not to be considered limiting of its scope. The invention will be described and explained with additional specificity and detail through the accompanying drawings in which.

DETAILED DESCRIPTION OF THE PREFERRED EMBODIMENTS

Figure 1:
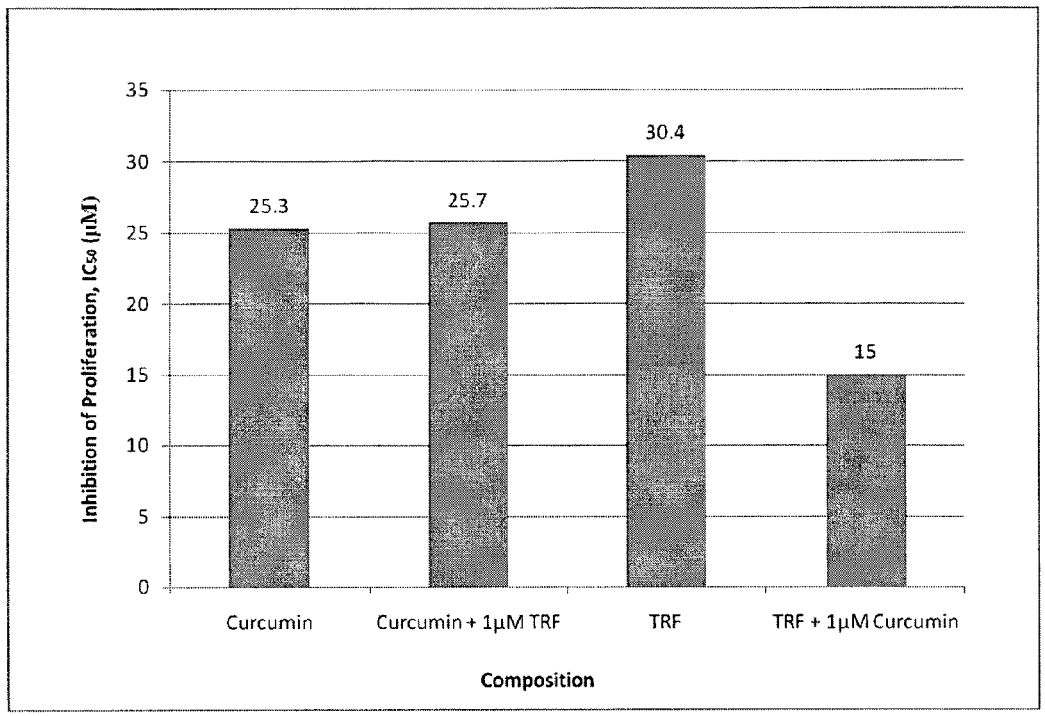
FIG. 1 shows inhibitory effects of TRF, Curcumin, Curcumin+1 µM TRF, TRF, and TRF+1 µM Curcumin on MCF-7 human breast cancer cells.
Figure 2:
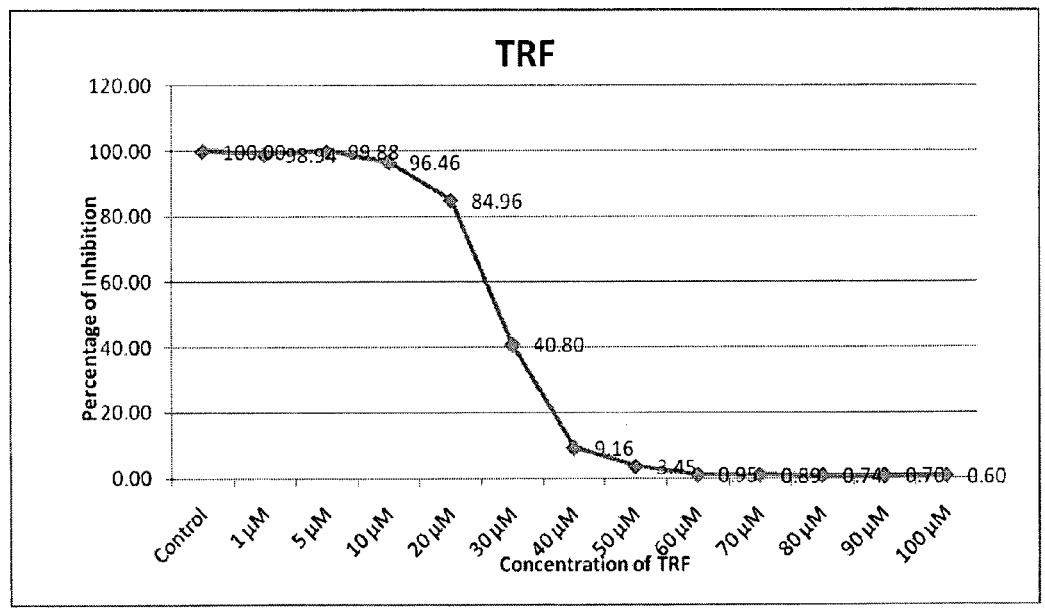
FIG. 2 shows the percentage of inhibition wherein the composition is composed only of TRF whose concentration is varied from 1 µM to 100 µM
Figure 3:
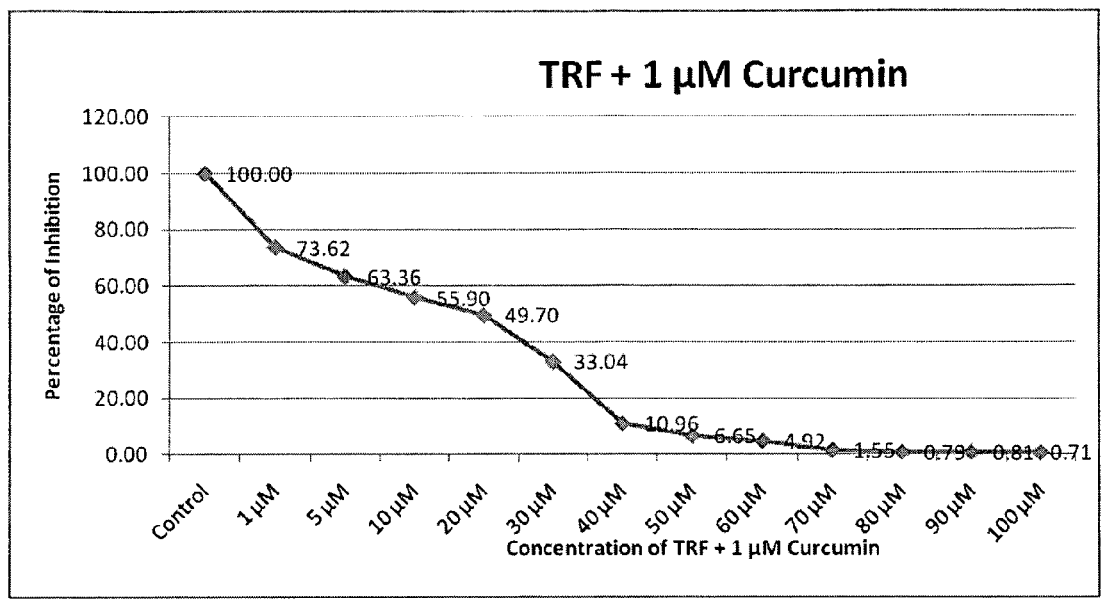
FIG. 3 shows the percentage of inhibition wherein the composition is composed of TRF whose concentration is varied from 1 µM to 100 µM and the concentration of Curcumin is 1 µM

The present invention relates to a transdermal fluid wherein the main ingredient is tocotrienol; and curcumin is the supporting ingredient. Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

In the present invention, the efficiency of curcumin when added to a composition with tocotrienol as the active ingredient is claimed.

METHOD

Tocotrienols and Curcumin Preparation

Stock solution of TRF and curcumin was prepared in dimethyl sulfoxide (DMSO) at a concentration of 10 mg/mL. For cell growth experiments (as described below), treatments of TRF and curcumin were diluted in phenol red-free RPMI 1640 medium supplemented with 5% dextran-charcoal-treated FCS (DCFCS) to final concentrations of 1-100 µM in test medium.

Cell Viability and Toxicity Assessment: Cell Growth Experiment

MCF-7 cells were suspended from T75 flask by treatment of trypsin to an equal volume of phenol red free RPMI 1640 medium supplemented with 5% dextran-charcoal treated FCS (DCFCS), 1% penicillin-streptomycin, 1% L-glutamine and counted on a haemocytometer. Cells were added to the required volume of phenol red free RPMI medium supplemented with 5% dextran-charcoal treated FCS (DCFCS), 1% penicillin-streptomycin, 1% L-glutamine. $0.5 \times 10^{-5}$ MCF-7 cells were seeded in each well of 24-well tissue culture dishes. After 24 hours, the medium was changed to various concentrations of test compounds (1-100 µM) prepared in phenol red free RPMI medium supplemented with 5% dextran-charcoal treated FCS (DCFCS), 1% penicillin-streptomycin, 1% L-glutamine, $10^{-8}$M estradiol. To examine the synergistic effects of curcumin and tocotrienols, a one to one combination of these compounds were incorporated into the test medium and tested on MCF-7 cells. For the cell viability count, cells were washed with 0.9% NaCl to wash off non-adherent dead cells, and were then lysed in 0.5 ml 0.01 M HEPES buffer/1.5 mM $MgCl_2$ plus 2 drops of zap-oglobin solution for 15 minutes. Cell proliferation was measured by using an automated particle counter, Beckman Coulter Particle Counter. Cell counts were taken by diluting 500 µL of cell solution sample in 10 mL lsoton. The nuclei released were counted in isoton on a Coulter particle counter. All cell counts were carried out in triplicate. Viable cell counts were taken after 72 hours.

Determination of $IC_{50}$ Using DPlot Software $IC_{50}$ curve for TRF, Individual Tocotrienols and a-Tocopherol was plotted using the DPlot graphing software. Based on the intersection value at 50%, accurate value was generated using the interpolate data feature of the DPlot software. The interpolate value was adjusted to 50 to obtain the $IC_{50}$ value and this generated for each replicates. The $IC_{50}$ value was calculated as an average of three generated value of each replicates.

Statistical Analysis

Comparisons between means of six groups were assessed for significance. In all cases, statistical significance was set at $P<0.05$, and data in the text, tables and figures are presented as means±SD.

TABLE 1

Inhibitory effects of TRF, Curcumin, Curcumin + 1 µM TRF, TRF, and TRF + 1 µM Curcumin on MCF-7 human breast cancer cells Inhibition of proliferation, $IC_{50}$:

| Curcumin | Curcumin + 1 µM TRF | TRF | TRF + 1 µM Curcumin |
|---|---|---|---|
| 25.3 µM | 25.7 µM | 30.4 µM | 15 µM |

Curcumin synergistically enhanced the anti-proliferative effect of tocotrienols on estrogen-positive MCF-7 human breast cancer cells in vitro.

The invention claimed is:

1. A composition consisting of an active amount of tocotrienol-rich fraction and curcumin and configured in a form that is administered topically, orally and subcutaneously, wherein the concentration of tocotrienol-rich fraction is 1 µM to 100 µM and the concentration of curcumin is 0.5 µM to 100 µM.

2. The composition of claim 1 wherein said tocotrienol-rich fraction comprises at least one of: α-tocotrienol, β-tocotrienol, γ-tocotrienol, and δ-tocotrienol.

3. A process of manufacturing a composition of claim 1 comprises the following steps:
   (a) preparing a stock solution of tocotrienol-rich fractions (TRF) and curcumin in dimethyl sulfoxide (DMSO); and
   (b) treating the stock solution of (a) by diluting the stock solution in phenol red-free RPMI 1640 medium supplemented with 5% dextran-charcoal-treated fetal calf serum (DCFCS).

4. The composition of claim 1 wherein the concentration of curcumin is 1 μM.

* * * * *